(12) United States Patent
Bruder et al.

(10) Patent No.: US 7,440,536 B2
(45) Date of Patent: Oct. 21, 2008

(54) METHOD FOR SCATTERED RADIATION CORRECTION OF A CT SYSTEM

(75) Inventors: Herbert Bruder, Höchstadt (DE); Martin Petersilka, Adelsdorf (DE); Rainer Raupach, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 50 days.

(21) Appl. No.: 11/543,836

(22) Filed: Oct. 6, 2006

(65) Prior Publication Data
US 2007/0086561 A1   Apr. 19, 2007

(30) Foreign Application Priority Data
Oct. 10, 2005   (DE) .................. 10 2005 048 397

(51) Int. Cl.
*G01N 23/00* (2006.01)
(52) U.S. Cl. ............................. 378/7; 378/4
(58) Field of Classification Search ............. 378/4, 378/7, 18, 19, 51, 70, 86
See application file for complete search history.

(56) References Cited
U.S. PATENT DOCUMENTS

| 6,639,964 B2 | 10/2003 | Schneider et al. |
| 6,876,719 B2 | 4/2005 | Ozaki |
| 6,980,626 B2 | 12/2005 | Groh et al. |
| 7,046,757 B1 * | 5/2006 | Bani-Hashemi et al. ........ 378/7 |

(Continued)

FOREIGN PATENT DOCUMENTS

DE   100 47 720 A1   4/2002

(Continued)

OTHER PUBLICATIONS

Siemens AG, H.Bruder, M.Petersilka: "Tomographiegerät zur schnellen Volumenabtastung eines Untersuchungsbereichs und Verfahren zur schnellen Volumenabtastung des Untersuchungsbereichs mit einem solchen Tomographiegerät", Mar. 30, 2005.

(Continued)

*Primary Examiner*—Irakli Kiknadze
(74) *Attorney, Agent, or Firm*—Harness, Dickey & Pierce, P.L.C.

(57) ABSTRACT

A method for scattered radiation correction of a CT system, including at least two focus/detector systems operated angularly offset from one another, is disclosed. In the method, at at least one phantom, similar to the examined object at least in a subregion, for at least one of the focus/detector systems, the scattered radiation intensity occurring is determined in the detector of a focus/detector system during the operation of the at least one focus of at least one other focus/detector system. Further, the spatial distribution thereof is stored for a number of angles of rotation of the focus/detector systems. During scanning of the object, the scattered radiation intensities, determined with the aid of a similar phantom that originate from the at least one other focus/detector system, are subtracted from the measured intensities of the first focus/detector system while taking account of the spatial orientation of the focus/detector systems and the beam respectively considered. Finally, absorption values are calculated with the aid of the intensity values thus corrected, and CT pictures or CT volume data are thereby reconstructed.

24 Claims, 5 Drawing Sheets

U.S. PATENT DOCUMENTS

| | | |
|---|---|---|
| 7,065,234 B2 * | 6/2006 | Du et al. .................... 382/131 |
| 7,190,758 B2 * | 3/2007 | Hagiwara ...................... 378/7 |
| 7,263,164 B2 * | 8/2007 | Ghelmansarai et al. ....... 378/87 |
| 2005/0025278 A1 | 2/2005 | Hagiwara |
| 2005/0078787 A1 | 4/2005 | Dinten et al. |
| 2006/0239396 A1 | 10/2006 | Bruder et al. |

FOREIGN PATENT DOCUMENTS

| | | |
|---|---|---|
| DE | 102 32 429 B3 | 1/2004 |
| DE | 103 02 565 A1 | 8/2004 |
| DE | 10 2005 014 853.0 A1 | 10/2006 |
| EP | 1 405 598 A1 | 4/2004 |
| EP | 1 502 548 A1 | 2/2005 |

OTHER PUBLICATIONS

German Office Action for corresponding case No. 10 2005 048 397.6.

* cited by examiner

METHOD FOR SCATTERED RADIATION CORRECTION OF A CT SYSTEM

PRIORITY STATEMENT

The present application hereby claims priority under 35 U.S.C. §119 on German patent application number DE 10 2005 048 397.6 filed Oct. 10, 2005, the entire contents of which is hereby incorporated herein by reference.

FIELD

The invention generally relates to a method for scattered radiation correction of a CT system having at least two simultaneously operated focus/detector systems. For example, it may relate to a method for a CT system including at least two simultaneously operated focus/detector systems arranged angularly offset from one another on a rotatable gantry, in which in order to scan an object the focus/detector systems arranged angularly offset from one another scan the object by virtue of the fact that they rotate about a system axis of the CT system and absorption values $a=-\ln(I/I_0)$ are determined for a multiplicity of individual rays S from the measured ratio of the measured radiation intensity I to the unattenuated radiation intensity $I_0$, the measured values are subjected to scattered radiation correction, and CT pictures or CT volume data of the object are reconstructed with the aid of the determined absorption data.

BACKGROUND

It is known in principle that during CT methods, scattered radiation effects are produced that lead to inaccuracies in the measurement of the absorption of X-radiation. Considering this effect, firstly, in the case of a single focus/detector system, the problem of scattered radiation becomes more severe here the wider the ray fan used is expanded, since the locations at which scattered radiation is produced increase correspondingly.

To counteract this known effect, there are fitted upstream of the detector in the case of such CT systems so-called scattered radiation collimators that uncover upstream of each detector element only the direct beam direction between detector element and focus, and largely shade all the other directions. Such scattered radiation collimators are also used in the case of two-focus or multifocus/detector systems. However, these scattered radiation collimators cannot reduce the scattered radiation that is produced by beams of another focus arranged in an angularly offset fashion, and that has the same spatial orientation as the actual direct beam that originates from a focus opposite the detector and whose intensity is to be measured.

There is thus the fundamental problem of determining the fraction of this scattered radiation in the overall measured intensity of the radiation, and of correcting the measured radiation intensity by this fraction so that the reconstruction uses actually only attenuation of the direct irradiation striking a detector element. Artifacts are otherwise produced in the CT display.

A known method for scattered radiation correction in a two-focus/detector system is disclosed, for example, in patent specification DE 102 32 429 B3. In the case of this patent specification, two focus/detector systems arranged angularly offset from one another are operated in an alternating fashion at least temporarily, such that the scattered radiation actually occurring and originating from the focus/detector system being operated can be measured directly in the focus/detector system respectively not switched on.

In order to carry out this method, it is necessary to operate the X-ray sources in an alternating fashion at least temporarily, as a result of which at these times image information from the CT scan is lacking at least in the detector of the X-ray tube that is not being operated, and so gaps are produced in the data acquisition. This is disadvantageous, particularly in the case of CT cardio pictures, which require a high time resolution, and this method leads in practice to deficient recording results.

SUMMARY

At least one embodiment of the invention is directed to a method for scattered radiation correction of a CT system having two focus/detector systems arranged angularly offset from one another, which method renders it possible to dispense with the direct measurement of the scattered radiation, and enables the scattered radiation fraction to be determined in continuous operation of the two focus/detector systems.

The inventors have realized that instead of measuring the scattered radiation fraction directly in a two-focus/detector system, it is more advantageous to determine the scattered radiation produced by the focus/detector system respectively arranged in an angularly offset fashion by taking measurements on a phantom or by simulation.

It is pointed out here that in the sense of at least one embodiment of the invention, a scattered radiation distribution is not to be understood simply as the spatial distribution of the scattered radiation generated by an object, but as the distribution arriving at a detector. Because of the scattered radiation collimators mentioned above, which are mostly used in CT detectors, and of the far reaching restriction, associated therewith, of the beam direction, this distribution can differ substantially from the scattered radiation produced at the object.

If this distribution of the scattered radiation is determined by measurement at the phantom, a CT scan of a phantom can be carried out with the aid of an active tube and data acquisition in the respective other focus/detector system, that is to say, for example: tube of the second focus/detector system FDSB active, and data acquisition in the first focus/detector system FDSA. Here, the scattering distribution for the second measuring system can also be obtained, given corresponding symmetry of the phantom, by reflecting the measured data at the logical middle of the detector. The number of channels of the second measuring system, which may be relatively low, thereby constitutes no restriction. The results of the measurement of the scattering distribution can be stored in lookup tables.

It is to be noted that the scattered radiation correction of the linear patient data is performed by subtracting the table entries scaled to the relevant current. A patient-specific selection of the lookup tables is described further below.

If, in another variant of an embodiment of the method, the scattered radiation is determined analytically, in particular by a computer simulation, for example by way of the Monte Carlo method for different body geometries, to this end a computer model of the human body is simulated with the aid of an active tube and data recording in the respective other DMS. The storage of the determined scattering distribution can likewise be performed in lookup tables in order to avoid excessively long computing times. Different tables are required for different body geometries, as the case may be.

It suffices to store the scattering distribution in a few angular directions in order to restrict the outlay on storage. It is possible to interpolate onto the angle array in the patient scan for later carrying out the correction of the patient data. It is advantageous to treat the angular dependence in the stationary coordinate system of the gantry.

The lookup tables prepared can, furthermore, be calibrated. To this end, the scattering distributions determined in a phantom measurement or a simulation are adapted by scaling for a selected body geometry. It is thereby possible to apply a scaling factor determined in this way to all the lookup tables. Moreover, the linear patient data can be corrected as a function of dose rate by subtracting the table entries scaled to the relevant tube current.

If correction tables exist for different shapes and sizes of phantoms, carrying out the method according to an embodiment of the invention requires a selection of the tables respectively suitable for the relevant patient, in particular for the relevant scanning cross section. This patient-specific selection of the lookup tables can be carried out, for example, as follows:

Firstly, it is possible to use a lateral and an ap-recorded (ap=anterior-posterior=from front to back) topogram, to determine the two principal axes of a cross section from this topogram, and to use them to estimate the relevant patient geometry in the respective scanning region.

On the other hand, it is possible to determine the maximum extent of the object at the considered projection angle even without a topogram from the measurement of measured value projections determined during the actual scan. It is possible here to take the average of the maximum extent of the object over all the detector rows, because the scattered radiation distribution is likewise averaged over the detector aperture.

A further variant resides in determining the characteristic position of an asymmetric transverse scattered radiation distribution on the basis of the positive difference values of oppositely directed and otherwise spatially identical beams through the same focus/detector system. Here, the profile of the scattered radiation distribution thus found can be compared with the profile of the scattered radiation distribution of previously determined scattering distributions at phantoms—at least over a particularly significant part of the profile—and the lookup table for which the scattering distributions of equal angle best correspond can be selected. Since data that had been sorted in parallel are assumed here, the scattering distributions of the lookup tables must likewise be stored in parallel geometry.

The simulation of only one model geometry is sufficient in principle. The position of the maximum of the asymmetric scattering distribution in the ap or in the lateral direction is approximately given by the patient dimensions. Consequently, the scattered radiation of the model geometry can be displaced by projection in accordance with the actual patient dimensions. If, for example, (l, b) (z) are the z-dependent dimensions of length and width, l and b, of the patient as determined using the method explained above, and $(l_M, b_M)(z)$ are the z-dependent dimensions of the model geometry, it is possible to use a suitable z-dependent channel displacement $\delta k$ in order to transform the model scattering distribution at the projection angle $\alpha$ into an estimated distribution of the patient scattering. The channel displacement $\delta k$ can, for example, be fashioned as follows:

$$\delta k(z) = (l(z) - l_M(z))/2 \cdot \Delta k,$$

$\delta k$ specifying the aperture of a detector channel at the center of rotation.

On the basis of these fundamental ideas of at least one embodiment of the invention as explained above, the inventors make a generalized proposal for improving a method for scattered radiation correction of a CT system having at least two simultaneously operated focus/detector systems, arranged angularly offset from one another on a rotatable gantry, in which in order to scan an object the focus/detector systems arranged angularly offset from one another scan the object by virtue of the fact that they rotate about a system axis of the CT system and absorption values $a = -\ln(I/I_0)$ are determined for a multiplicity of individual rays S from the measured ratio of the measured radiation intensity I to the unattenuated radiation intensity $I_0$, the measured values are subjected to scattered radiation correction, and CT pictures or CT volume data of the object are reconstructed with the aid of the determined absorption data. The improvement resides in the fact that at at least one phantom, similar to the examined object at least in a subregion, for at least one of the focus/detector systems the scattered radiation intensity $I_{AS}$ occurring is determined in the detector of a focus/detector system during the operation of the at least one focus of at least one other focus/detector system, and the spatial distribution thereof is stored for a number of angles of rotation of the focus/detector systems, during scanning of the object the scattered radiation intensities $I_{AS}$ determined with the aid of a similar phantom that originate from the at least one other focus/detector system are subtracted from the measured intensities $I_{AS}$ of the first focus/detector system while taking account of the spatial orientation of the focus/detector systems and the beam respectively considered, and the absorption values $a_{korr} = -\ln(I'/I_0)$ are calculated with the aid of the intensity values I' thus corrected, and CT pictures or CT volume data are thereby reconstructed.

At least one embodiment of this method can be used in principle for scanning any desired objects, but it is particularly suitable in the examination of patients, in particular for cardio examinations, where the temporal resolution of the CT is improved by the relatively large number of focus/detector systems.

In one design of an embodiment of the method, a computer simulation of the scattered radiation occurring can be carried out in order to determine the scattered radiation intensity $I_{AS}$ in at least one focus/detector system, or the scattered radiation occurring can be measured directly in order to determine the scattered radiation intensity $I_{AS}$ in the at least one focus/detector system.

Alternatively, the scattered radiation distribution can be determined in all the focus/detector systems.

If the scattered radiation distribution of all the focus/detector systems is to be determined, in addition to the possibility of measuring this directly at a phantom or of obtaining it analytically by appropriate calculations, it is also possible in the case of a symmetrical phantom, after the determination of the scattered radiation distribution in a first focus/detector system to obtain the scattered radiation distribution in a second focus/detector system by reflecting the scattered radiation distribution of the first focus/detector system over the channels and transmitting it to the second focus/detector system.

It is also advantageous when the scattered radiation distribution for a number of different phantoms similar to an object is determined and stored, and the scattered radiation intensities $I_{AS}$ and $I_{BS}$ of a phantom which is as close as possible in shape, size and composition are selected for the purpose of scattered radiation correction as a function of the current scanning region.

It is advantageous to this end when in order to select a data record of scattered radiation correction values $I_{AS}$ and $I_{BS}$ a topogram of the object to be scanned is recorded in at least one plane, preferably in planes that correspond to the angular offset of the focus/detector systems used, the extent of the object in the scanning region is determined therefrom, and a data record is used for the scattered radiation correction of a phantom of similar extent.

Alternatively, it can also be advantageous when in order to select a data record of scattered radiation correction values $I_{AS}$ and $I_{BS}$, the size of the scanned object is determined by means of the attenuation of the beams of at least one projection in at least one plane, preferably in a number of planes, and the extent of the object in the scanning region is determined therefrom and a data record is used for the scattered radiation correction of a phantom of similar extent.

Since the phantom measurements cannot be carried out in practice for any desired large number, it is necessary for the existing scattered radiation distributions of available phantom measurements to be adapted to the actual size relationships of the scanned object or the patient. This can be done by interpolating the scattered radiation values and their channel designations of available neighboring phantom variables.

On the other hand, it is also possible to make a fit with the actual object dimensions starting from a few phantoms by scaling the scattered radiation values and their channel designations of an available phantom.

Instead of directly determining the size of the scanned object, or of determining the size relationships via topograms or the attenuation profile of projections and directly inferring the extent of the object or patient, an approximate scattered radiation profile can be determined with the aid of the scan data of the object, this being done by using the intensity values of direct parallel projections to determine the intensity values of complementary parallel projections of the same focus/detector systems. The positive excesses of the intensity values of the direct parallel projections are determined by channel and evaluated as approximate scattered radiation fractions. Subsequently, for the purpose of scattered radiation correction a stored data record of scattered radiation correction values of a phantom that varies most similarly to the directly measured scattered radiation profile, at least with reference to a subregion of the parallel projection, is used.

Existing data records of scattered radiation correction values can also be adapted to the actual relationships of the relevant scan by virtue of the fact that before use is made of a data record of scattered radiation correction values of a phantom with a known object shadow at at least one projection angle, the object shadow of the scanned object is determined at at least one such projection angle, and this data record of scattered radiation correction values is scaled and/or displaced in accordance with the measured extent of the current object shadow.

Furthermore, the values of the scattered radiation distribution for nonexistent spatial beams or channels of the respective detector can be determined by interpolation of neighboring existing values.

It is also advantageous to normalize the scattered radiation correction to the tube currents used in the system respectively generating scattered radiation, and to use correction values adapted thereto when correcting scattered radiation in accordance with the tube current actually existing.

With reference to the reconstruction performed subsequent to the scattered radiation correction, no restrictions result with reference to known reconstruction methods with the aid of single or multiple focus/detector systems. Thus, it is possible to use exclusively absorption data of the same focus/detector system for the reconstruction, or to mix absorption data of all or both focus/detector systems.

As a rule, a calibration, in particular an air calibration and/or a normalization to a dose monitor value and/or a radiation hardening correction and/or a channel correction and/or a water scaling have been carried out before the scattered radiation correction is carried out for each focus/detector system.

It is also advantageous to normalize the focus/detector systems to one another, particularly when the data of the focus/detector systems are to be mixed for the reconstruction.

In accordance with the previously described method and its designs and modifications, the inventors also propose, in at least one embodiment, a CT system having at least two simultaneously operated focus/detector systems arranged angularly offset from one another on a rotatable gantry and at least one control and computation unit having computer programs that control the operation of the CT system and reconstruct CT images or CT volume data, wherein at least one computer program includes a program code that when executed simulates the method steps of at least one of the preceding method claims.

BRIEF DESCRIPTION OF THE DRAWINGS

The invention is described in more detail below using the example embodiments and with the aid of the figures, only the features required for understanding the invention being illustrated. The following reference numerals are used here: 1: CT system; 2: first focus of the FDSA; 3: first detector system of the FDSA; 4: second focus of the FDSB; 5: second detector system of the FDSB; 6: gantry housing; 7: patient; 8: displaceable patient couch; 9: system axis; 10: control and computation unit; 11: ray fan of the X-ray tube 2; 12: ray fan of the X-ray tube 4; 13: intensity profile of the scattered radiation of a direct projection p; 14: channelwise difference between a direct and a complementary projection p and p'; $Prg_1$ -$Prg_n$: computer programs for executing the method according to the invention; I: intensity; $I_0$: initial intensity; S: direct ray; S': complementary ray; $F_A$: focus of the focus/detector system FDSA; $F_B$: focus of the second focus/detector system FDSB; $D_A$: detector of the focus/detector system FDSA; $D_B$: detector of the focus/detector system FDSB; Δ: scattered radiation fraction of the complementary beam S'; k: channel number; K: scattered radiation collimator; P: phantom; $β_A$: fan angle of the focus/detector system FDSA; $β_B$: fan angle of the focus/detector system FDSB.

In detail.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
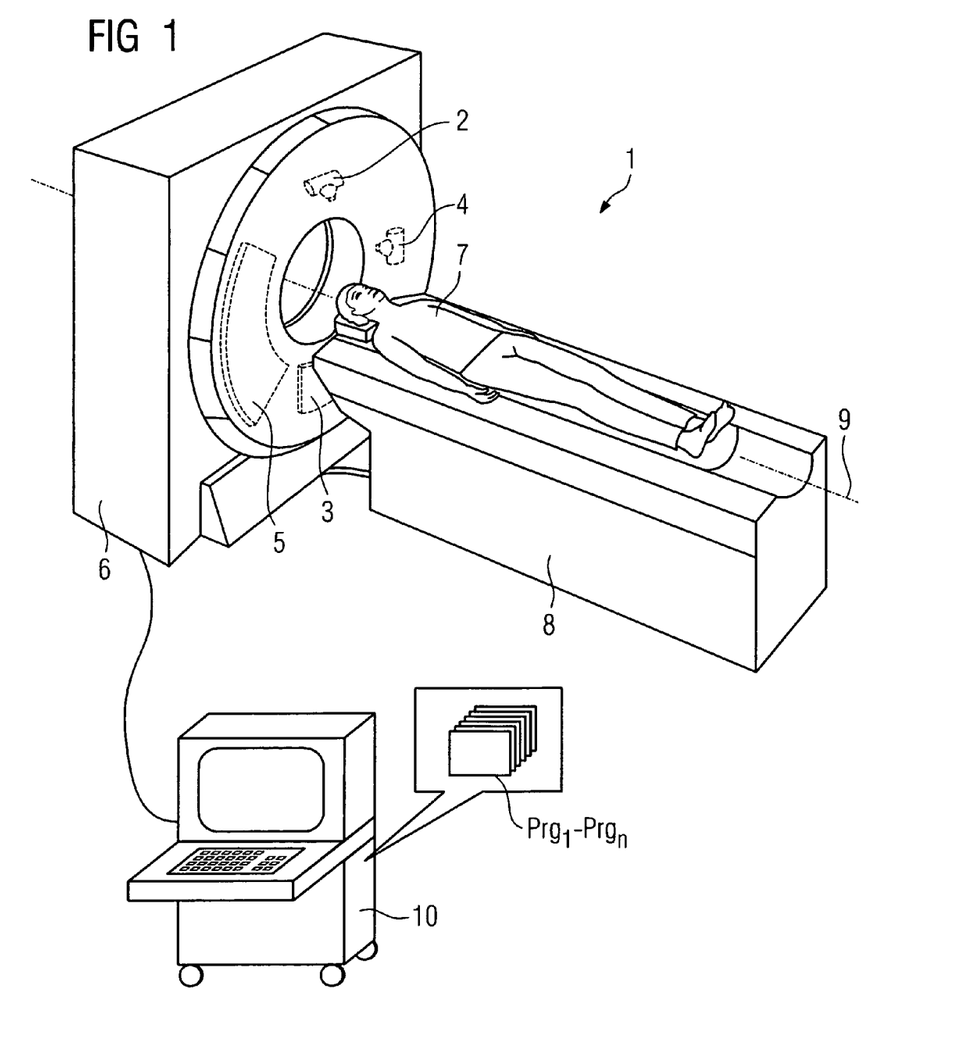
FIG. 1 shows a 3D schematic of a CT system having two focus/detector systems arranged in an angularly offset fashion.

FIG. 1 shows an example computed tomography system 1 having two focus/detector systems having a first focus/detector system FDSA with a first X-ray tube 2 and a detector 3 situated opposite, and a second focus/detector system FDSB to which the second X-ray tube 4 and the detector 5 situated opposite belong. The focus/detector systems 2, 3 and 4, 5 are arranged angularly offset by 90° on a gantry (not illustrated explicitly) in the gantry housing 6, and are moved during scanning of the patient about the system axis 9, while the patient 7 is pushed continuously or sequentially through the scanning region. This purpose is served by a patient couch 8 that can be displaced longitudinally and is driven by the control and computation unit 10.

The control and computation unit 10 is also responsible for controlling and operating the gantry with the two focus/detector systems 2, 3 and 4, 5. Moreover, the absorption data that are obtained by the two focus/detector systems are collected in this control and computation unit 10 and can also be converted thereby by way of the reconstruction method (known per se) into CT image data records or CT volume data records. The programs $Prg_1$ to $Prg_n$ illustrated by way of example and in which the method steps according to at least one embodiment of the invention are also depicted are used to this end.

Figure 2:
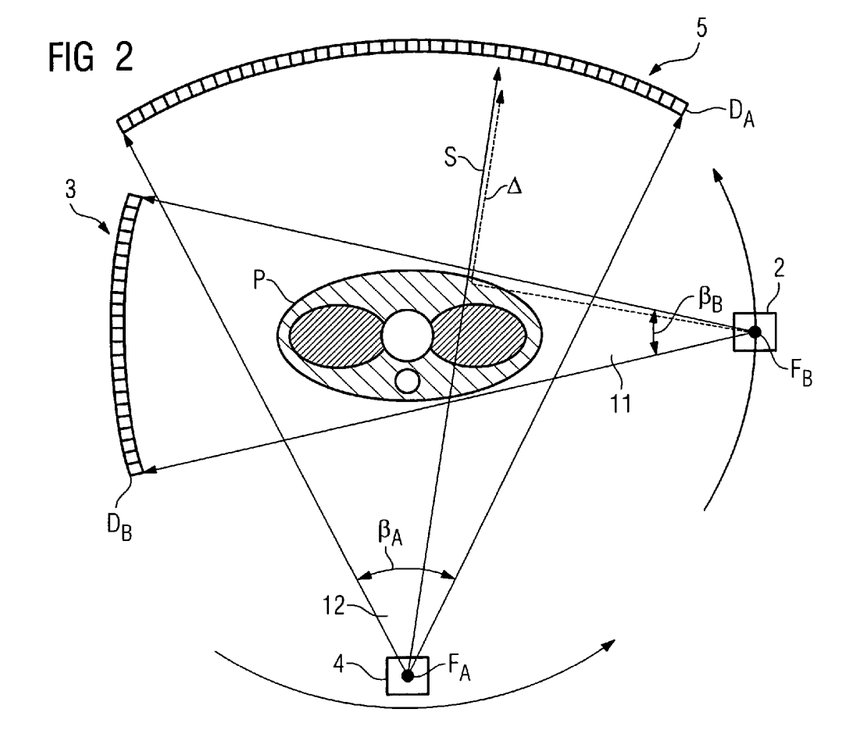
FIG. 2 shows a schematic of a cross section through a CT system in accordance with FIG. 1.

The schematic of FIG. 2 serves for better understanding of the problems of transverse scattering in such a CT system with two focus/detector systems. A phantom P is illustrated which has a coarse inner structure that is scanned by the two focus/detector systems FDSA with the focus $F_A$ and the detector $D_A$, and the focus/detector system FDSB, arranged offset therefrom by 90°, with the focus $F_B$ and the detector $D_B$. The two assigned X-ray tubes 4 and 2 in which the foci $F_A$ and $F_B$ are located are shown for a better orientation with reference to FIG. 1. The detectors $D_A$ and $D_B$, which are illustrated here only as a row of detector elements, are assigned the reference numerals 5 and 3, respectively. The fan angles of the ray fans used are represented by $\beta_A$ and $\beta_B$, the beam cones 12 and 11 being formed from the foci $F_A$ and $F_B$, respectively. Arrows specify the direction of revolution of the two focus/detector systems.

Figure 3:
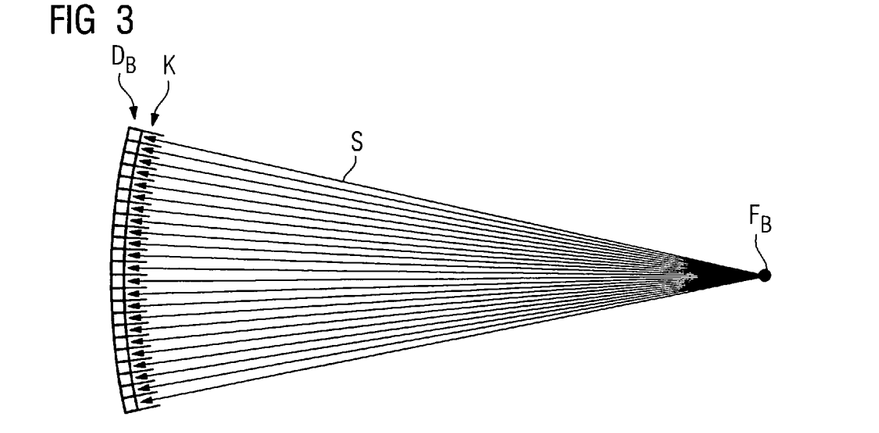
FIG. 3 shows a cross section through a focus/detector system having a scattered radiation collimator.

It is seen from a consideration of a direct ray emanating from the focus $F_A$ toward a detector element of the detector $D_A$ that if both focus/detector systems are in operation, a scattered radiation Δ simultaneously occurs that likewise makes a contribution to the measured intensity at the same detector element at which the intensity I of the ray S is measured. If, as is illustrated in FIG. 3 with reference to the example of the focus/detector system FDSB having the focus $F_B$ and the detector $D_B$, a scattered radiation collimator K is arranged on the ray side upstream of the detectors, the only rays that can advance unattenuated to the detector elements are those with approximately the same ray direction as exhibited by the direct rays S from the oppositely situated focus $F_B$ to the respective detector element of the detector $D_B$. Other ray directions are largely absorbed by the collimator K.

Figure 4:
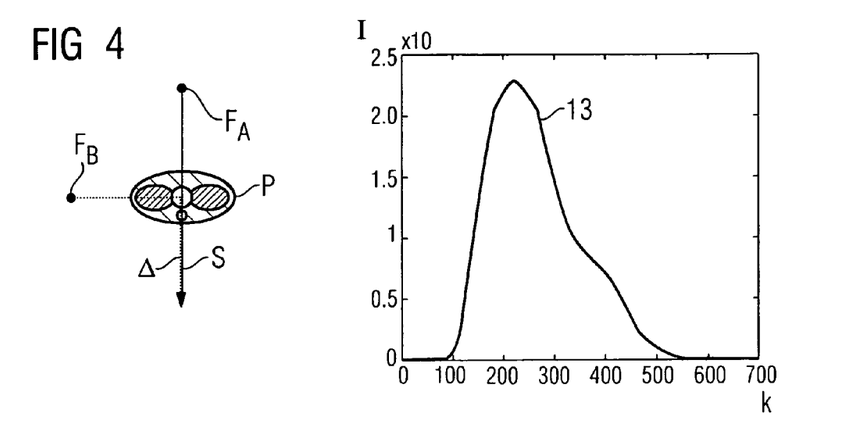
FIGS. 4-6 show the scattered radiation distribution for parallel projection in different focus/detector positions.
Figure 5:
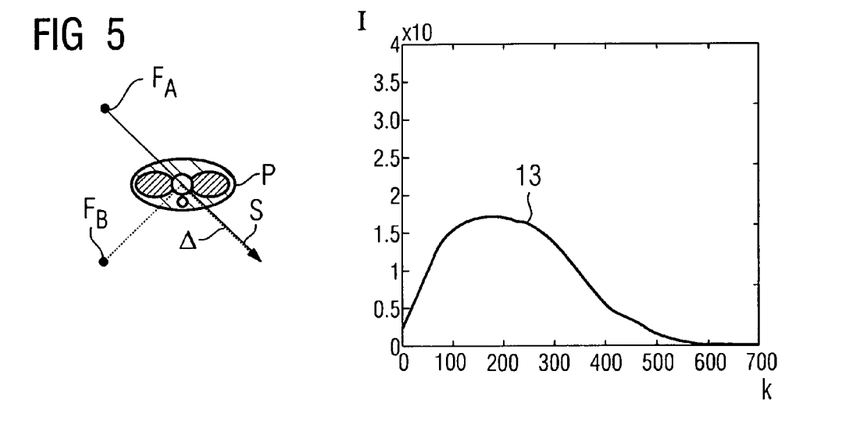
Figure 6:
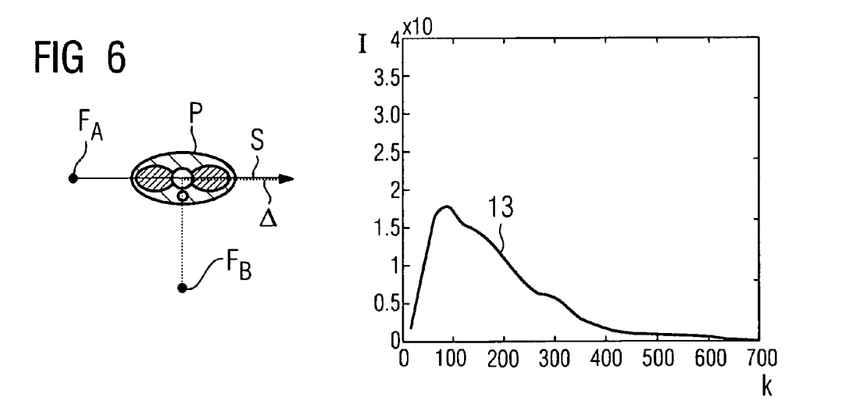

Since the patient being examined and, correspondingly, also a similar phantom are not exactly rotationally symmetric as a rule, it also follows that the scattered radiation produced thereat is a function of the angular position of the considered focus/detector systems, and is also a function of channel in the case of parallel projections considered. An example of such a scattered radiation distribution and its dependence on angle and channel in the case of parallel projections is shown in FIGS. 4-6.

Indicated on the left in each figure is the angular position of the projection shown together with the orientation of the two foci and the direct ray direction with the continuous line, on the one hand, and the ray, represented by dots and generating scattered radiation, with its scattered ray, on the other hand. Plotted on the right in each case in the graphs is the calculated profile 13 of the scattered radiation intensity of a parallel projection of this direction and orientation of the foci. Here, the channel number is plotted on the abscissa and the intensity of the scattered radiation arriving at the detector element is plotted on the ordinate.

If such curves are available on call as a function of the shape and size of the phantom, it is possible according to an embodiment of the invention for this known scattered radiation fraction to be subtracted from the measured intensities, and the effect of the direct rays S is exclusively obtained as intensity value. However, attention should also be given to the possible effect on the determined scattered radiation profiles of changed tube currents.

Just as the distribution of the scattered radiation can be determined in an analytical way, it is also possible according to an embodiment of the invention to carry out a direct measurement of the scattered radiation distribution at one or more phantoms, and to carry out the scattered radiation correction using these values.

The adaptation of available scattered radiation distributions of known phantom sizes and shapes to the actual sizes and shapes of the scanned patient can, on the one hand, take place by means of scalings or interpolation, it being possible, for example, to determine the dimensions of the patient by topogram.

On the other hand, it is possible to use a scattered radiation distribution measured approximately directly at the patient to select the phantom suitable therefor retroactively, and then to use these values for the scattered radiation direction.

The inventors, in at least one embodiment, have come to realize that the principal fraction of the scattered radiation emanates substantially from the surface layer of the scanned object and does not originate from the deep layers of the patient. These geometric relationships give rise to the typical asymmetric profile, dependent on the shape and size of the object, of the scattered radiation in a parallel projection.

Figure 7:
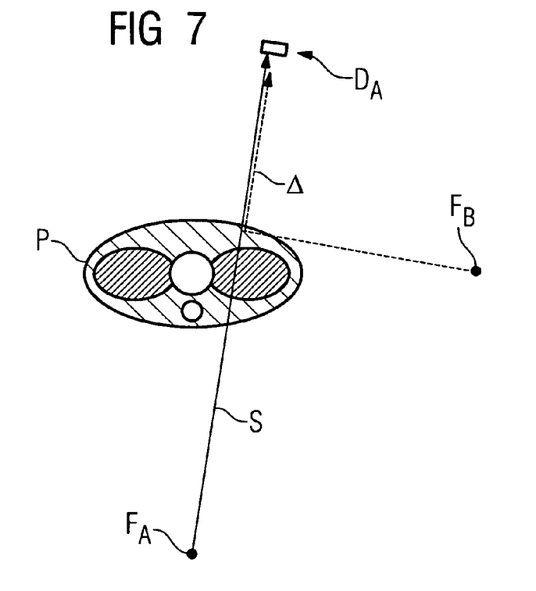
FIG. 7 shows a simplified illustration of a direct ray through a patient with a simultaneous scattered radiation fraction from the angularly offset focus.
Figure 8:
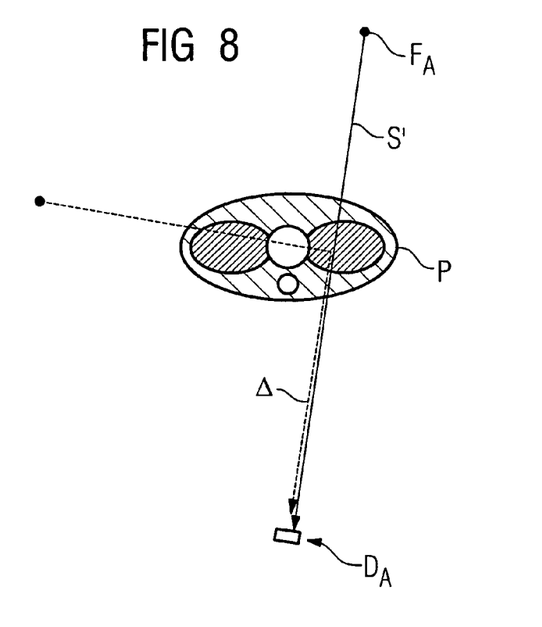
FIG. 8 shows an illustration from FIG. 3, but angularly offset by 180°.

Considering now an individual direct scanning ray S in FIG. 7 and the complementary scanning ray S' in FIG. 8, which run in a fashion emanating from a focus $F_A$ to a detector element of the detector $D_A$, the measured intensity I would have to be identical in each case. However, since, principally in the situation of FIG. 7, scattered radiation Δ reaches the detector and the intensity measurement is falsified so as to increase the value, the scattered radiation fraction results in each case from the positive difference between the rays. If this scattered radiation fraction thus measured is plotted against the channels in a parallel projection, the result is a profile 14 such as is illustrated in FIG. 9.

Figure 9:
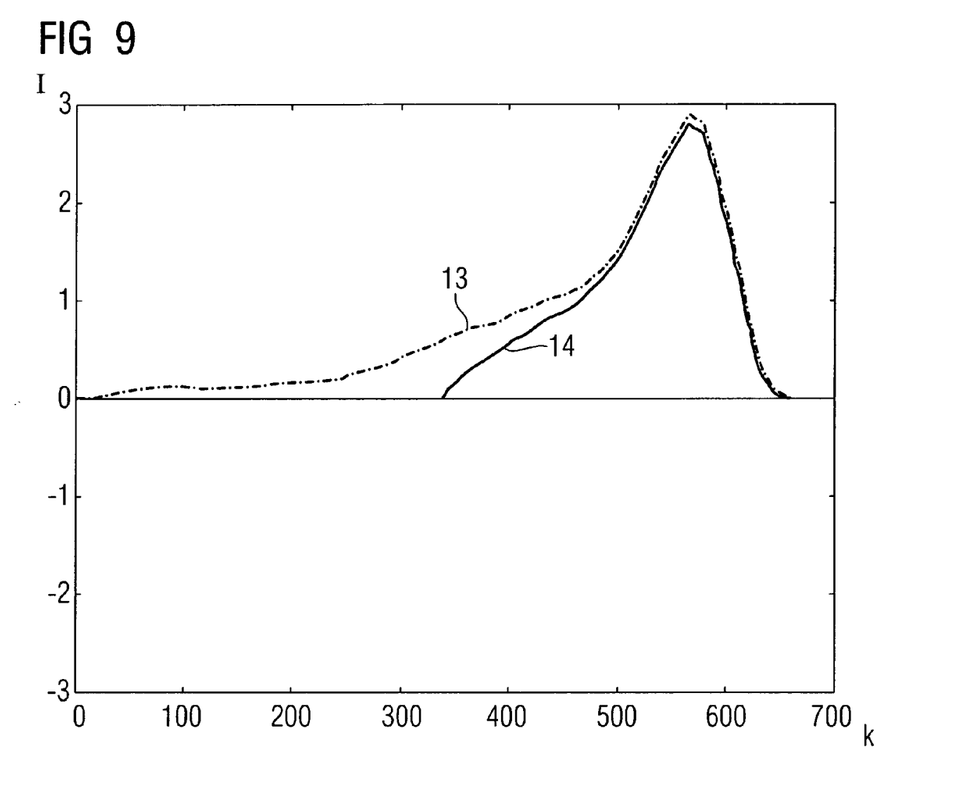
FIG. 9 shows an actual profile, determined by a differential measurement, of the scattered radiation fraction of a projection.

At the same time, the profile 13 of the actual scattered radiation distribution is shown in FIG. 9. Considering the two curves, it is to be seen in the right-hand part, substantially at the rising edge and, as the case may be, up to half the height of the left-hand edge, that the curves largely correspond here. The difference, becoming ever larger to the left, between the actual scattered radiation distribution 13 and the scattered radiation distribution 14 determined over oppositely directed rays is based on the fact that the oppositely directed rays also have a scattered radiation fraction which, however, runs in mirror-image fashion. From the right to the middle of the projection, this scattered radiation fraction thus increases in the case of the complementary rays, and thereby increasingly compensates the scattered radiation fraction of the direct rays. For this reason, it is only the profile of the right-hand fraction that is useful for comparison with the profiles that originate from phantom measurements or phantom calculations.

It is self-evident that the above-named features of embodiments of the invention can be used not only in the respectively specified combination, but also in other combinations or on their own, without departing from the framework of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scattered radiation correction of a CT system including at least two simultaneously operated focus/detector systems, arranged angularly offset from one another on a rotatable gantry, the method comprising:
    scanning an object by rotating the focus/detector systems, arranged angularly offset from one another, about a system axis of the CT system;
    determining absorption values for a multiplicity of individual rays from a measured ratio of measured radiation intensity from the scanning to unattenuated radiation intensity;
    subjecting the determined absorption values values to a scattered radiation correction;
    reconstructing at least one of CT pictures and CT volume data of the object using the determined absorption values, wherein,
    using at least one phantom, similar to the examined object at least in a subregion, for at least one of the focus/detector systems, a scattered radiation intensity occurring is determined in a detector of one of the at least two focus/detector systems during the operation of at least one focus of at least one other focus/detector system, and a spatial distribution thereof is stored for a number of angles of rotation of the focus/detector systems, wherein
    during scanning of the object, the scattered radiation intensities determined with the aid of a similar phantom that originate from the at least one other focus/detector system are subtracted from the measured intensities of the at least one of the focus/detector systems system while taking account of a spatial orientation of the focus/detector systems and a beam respectively considered, and wherein
    the absorption values are calculated with the aid of the intensity values thus corrected, and at least one of the CT pictures and the CT volume data are thereby reconstructed.

2. The method as claimed in claim 1, wherein a computer simulation of the scattered radiation occurring is carried out in order to determine the scattered radiation intensity in at least one focus/detector system.

3. The method as claimed in claim 1, wherein the scattered radiation occurring is measured directly in order to determine the scattered radiation intensity in at least one focus/detector system.

4. The method as claimed in claim 1, wherein the scattered radiation distribution is determined in all the focus/detector systems.

5. The method as claimed in claim 4, wherein, in the case of a symmetrical phantom, after the determination of the scattered radiation distribution in a first focus/detector system, the scattered radiation distribution in a second focus/detector system is determined by reflecting the scattered radiation distribution of the first focus/detector system over the channels and transmitting it to the second focus/detector system.

6. The method as claimed in claim 5, wherein size differences between the object actually to be scanned and the existing phantoms are compensated by scaling the scattered radiation values and their channel designations of an available phantom.

7. The method as claimed in claim 1, wherein the scattered radiation distribution for a number of different phantoms similar to an object is determined and stored, and the scattered radiation intensities of a phantom, which is as close as possible, are selected for the purpose of scattered radiation correction as a function of the relevant scanning region.

8. The method as claimed in claim 7, wherein, in order to select a data record of scattered radiation correction values, a topogram of the object to be scanned is recorded in at least one plane and the extent of the object in the scanning region is determined therefrom, and a data record is used for the scattered radiation correction of a phantom of similar extent.

9. The method as claimed in claim 7, wherein, in order to select a data record of scattered radiation correction values, the size of the scanned object is determined via the attenuation of the beams of at least one projection in at least one plane, and the extent of the object in the scanning region is determined therefrom and a data record is used for the scattered radiation correction of a phantom of similar extent.

10. The method as claimed in claim 7, wherein size differences between the object actually to be scanned and the existing phantoms are compensated by interpolating the scattered radiation values and their channel designations of available neighboring phantom sizes.

11. The method as claimed in claim 7, wherein, in order to select a data record of scattered radiation correction values, an approximate scattered radiation profile is determined with the aid of the scan data of the object, this being done by using positive intensity fractions of direct parallel projections to determine the intensity values of complementary parallel projections of the same focus/detector system, and by using for the purpose of scattered radiation correction a stored data record of scattered radiation correction values of a phantom that varies most similarly to the directly arranged scattered radiation profile, at least with reference to a subregion of the parallel projection.

12. The method as claimed in claim 7, wherein, in order to select a data record of scattered radiation correction values, a topogram of the object to be scanned is recorded in planes that correspond to the angular offset of the focus/detector systems used, and the extent of the object in the scanning region is determined therefrom, and a data record is used for the scattered radiation correction of a phantom of similar extent.

13. The method as claimed in claim 7, wherein, in order to select a data record of scattered radiation correction values, the size of the scanned object is determined via the attenuation of the beams of at least one projection in a number of planes, and the extent of the object in the scanning region is determined therefrom and a data record is used for the scattered radiation correction of a phantom of similar extent.

14. The method as claimed in claim 1, wherein, before use is made of a data record of scattered radiation correction values of a phantom with a known object shadow of at least one projection angle, the object shadow of the scanned object is determined of at least one such projection angle, and this data record of scattered radiation correction values is at least one of scaled and displaced in accordance with the measured extent of the current object shadow.

15. The method as claimed in claim 1, wherein the values of the scattered radiation distribution for nonexistent spatial beams or channels of the respective detector are determined by interpolation of neighboring existing values.

16. The method as claimed in claim 1, wherein the scattered radiation correction is normalized to tube currents used and adapted in accordance with the actual existing tube currents.

17. The method as claimed in claim 1, wherein absorption data of the same focus/detector system are exclusively used for the reconstruction.

18. The method as claimed in claim 1, wherein absorption data of the two focus/detector systems are mixed for the reconstruction.

19. The method as claimed in claim 1, wherein a calibration is carried out before the scattered radiation correction is carried out for each focus/detector system.

20. The method as claimed in claim 1, wherein the focus/detector systems are normalized to one another before the scattered radiation correction is carried out.

21. A CT system, comprising:
at least two simultaneously operated focus/detector systems, arranged angularly offset from one another on a rotatable gantry; and
at least one control and computation unit to run at least one computer program to control an operation of the CT system and reconstruct at least one of CT images and CT volume data, at least one computer program including program code that, when executed, simulates the method of claim 1.

22. The method as claimed in claim 1, wherein at least one of an air calibration, a normalization to a dose monitor value, a radiation hardening correction, a channel correction and a water scaling is carried out before the scattered radiation correction is carried out for each focus/detector system.

23. A computer readable medium including program segments for, when executed on a computer device, causing the computer device to implement the method of claim 1.

24. A CT system, comprising:
at least two simultaneously operated focus/detector systems, arranged angularly offset from one another on a rotatable gantry, to scan an object by rotating the focus/detector systems;
means for determining absorption values for a multiplicity of individual rays from a measured ratio of measured radiation intensity from the scanning to unattenuated radiation intensity;
means for subjecting the determined absorption values to scattered radiation correction; and
means for reconstructing at least one of CT pictures and CT volume data of the object using the determined absorption values, wherein,
using at least one phantom, similar to the examined object at least in a subregion, for at least one of the focus/detector systems a scattered radiation intensity occurring is determined in a detector of the at least two focus/detector systems during the operation of the at least one focus of at least one other focus/detector system and a spatial distribution thereof is stored for a number of angles of rotation of the focus/detector systems, wherein
during scanning of the object, the scattered radiation intensities determined with the aid of a similar phantom that originate from the at least one other focus/detector system are subtracted from the measured intensities of the first focus/detector system while taking account of a spatial orientation of the focus/detector systems and a beam respectively considered, and wherein the absorption values are calculated with the aid of the intensity values thus corrected, and at least one of the CT pictures and the CT volume data are thereby reconstructed.

* * * * *